United States Patent
Olsen et al.

(12) 
(10) Patent No.: US 6,232,100 B1
(45) Date of Patent: May 15, 2001

(54) CORTISTATIN POLYPEPTIDES

(75) Inventors: Henrik S. Olsen, Gaithersburg; Steven M. Ruben, Olney, both of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/001,472

(22) Filed: Dec. 31, 1997

Related U.S. Application Data

(60) Provisional application No. 60/037,386, filed on Feb. 7, 1997, and provisional application No. 60/033,980, filed on Dec. 31, 1996.

(51) Int. Cl.[7] .............................. C12N 1/21; C12N 5/10; C12N 15/12; C12N 15/63
(52) U.S. Cl. ................. 435/69.4; 435/69.1; 435/455; 435/471; 435/325; 435/252.3; 536/23.1; 536/23.5; 536/23.51
(58) Field of Search .................... 435/69.1, 69.4, 435/455, 471, 325, 252.3; 536/23.1, 23.5, 23.51

(56) References Cited

U.S. PATENT DOCUMENTS

| | | | |
|---|---|---|---|
| 5,466,593 | * 11/1995 | Shimomura et al. | 435/219 |
| 6,074,872 | 6/2000 | Sutcliffe et al. | 435/325 |

FOREIGN PATENT DOCUMENTS

| | | |
|---|---|---|
| WO 89/01945 | * 3/1989 | (WO) . |
| WO 97/43417 | 11/1997 | (WO) . |
| WO 97/46668 | 12/1997 | (WO) . |

OTHER PUBLICATIONS

Wells, Biochemistry 29:8509–8517, 1990.*

Ngo et al., The Protein Folding Problem and Tertiary Structure Prediction, Merz et al., eds., Birkhauser, Boston, pp. 492–495, 1994.*

Schulz et al., Principles of Protein Structure, Springer–Verlag, New York, pp. 14–16, 1979.* de Lecea, L. et al., "Cloning, mRNA Expression, and Chromosomal Mapping of Mouse and Human Preprocortistatin," *Genomics* 42:499–506 (Jun. 1997).

Tostivint, H. et al., "Un deuxième gène codant pour la somatostatine est exprimé dans le cerveau," *Medecine Sci.* 12:1131–1133 (Oct. 1996).

Tostivint, H. et al., "Occurrence of two somatostatin variants in the frog brain: Characterization of th cDNAs, distribution of the mRNAs, and receptor–binding affinities of the peptides," *Proc. Natl. Acad. Sci. USA* 93:12605–12610 (Oct. 1996).

Fukusumi, S. et al., "Identification and Characterization of a Novel Human Cortistatin–like Peptide," *Biochem. & Biophys. Res. Comm.* 232:157–163 (Mar. 1997).

de Lecea, L. et al., "A cortical neuropeptide with neuronal depressant and sleep–modulating properties," *Nature* 381:242–245 (May 1996).

NCBI Entrez, GenBank Report, Accession No. W79063, from Hillier, L. et al., (Oct. 1996), with Revision History.

NCBI Entrez, GenBank Report, Accession No. AA719497, from Hillier, L. et al. (Dec. 1997), with Revision History.

NCBI Entrez, GenBank Report, Accession No. AB000263, from Fukusumi, S. (Apr. 1997), with Revision History.

* cited by examiner

*Primary Examiner*—Elizabeth Kemmerer
(74) *Attorney, Agent, or Firm*—Sterne, Kessler, Goldstein & Fox P.L.L.C.

(57) ABSTRACT

The present invention relates to novel cortistatin polypeptides, and to polynucleotides encoding these polypeptides. More specifically, isolated nucleic acid molecules are provided encoding a Human Cortistatin polypeptide. Cortistatin polypeptides are also provided, as are vectors, host cells and recombinant methods for producing the same. Also provided are diagnostic methods for detecting variations in Human Cortistatin gene expression and therapeutic methods for treating individuals in need of an increased level of Human Cortistatin activity.

50 Claims, 3 Drawing Sheets

```
    AAGAGCAGCAGCAGGGTGGGAGAGAAGCTCCAGTCAGCCCACAAGATGCCATTGTCCCCC
  1 ---------+---------+---------+---------+---------+---------+  60
                                                  MetProLeuSerPro
                                                   M   P   L   S   P

GGCCTCCTGCTGCTGCTGCTCTCCGGGGCCACGGCCACCGCTGCCCTGCCCCTGGAGGGT
 61 ---------+---------+---------+---------+---------+---------+ 120
    GlyLeuLeuLeuLeuLeuLeuSerGlyAlaThrAlaThrAlaAlaLeuProLeuGluGly
     G   L   L   L   L   L   L   S   G   A   T   A   T   A   A   L   P   L   E   G

GGCCCCACCGGCCGAGACAGCGAGCATATGCAGGAAGCGGCAGGAATAAGGAAAAGCAGC
121 ---------+---------+---------+---------+---------+---------+ 180
    GlyProThrGlyArpAspSerGluHisMetGlnGluAlaAlaGlyIleArgLysSerSer
     G   P   T   G   R   D   S   E   H   M   Q   E   A   A   G   I   R   K   S   S

CTCCTGACTTTCCTCGCTTGGTGGTTTGAGTGGACCTCCCAGGCCAGTGCCGGGCCCCTC
181 ---------+---------+---------+---------+---------+---------+ 240
    LeuLeuThrPheLeuAlaTrpTrpPheGluTrpThrSerGlnAlaSerAlaGlyProLeu
     L   L   T   F   L   A   W   W   F   E   W   T   S   Q   A   S   A   G   P   L

ATAGGAGAGGAAGCCCGGGAGGTGGCCAGGCGGCAGGAAGGCGCACCCCCCCAGCAATCT
241 ---------+---------+---------+---------+---------+---------+ 300
    IleGlyGluGluAlaArgGluValAlaArgArgGlnGluGlyAlaProProGlnGlnSer
     I   G   E   E   A   R   E   V   A   R   R   Q   E   G   A   P   P   Q   Q   S

GCGCGCCGGGACAGAATGCCCTGCAGGAACTTCTTCTGGAAGACCTTCTCCTCCTGCAAA
301 ---------+---------+---------+---------+---------+---------+ 360
    AlaArgArgAspArgMetProCysArgAsnPhePheTrpLysThrPheSerSerCysLys
     A   R   R   D   R   M   P   C   R   N   F   F   W   K   T   F   S   S   C   K

TAAAACCTCACCCATGAATGCTCACGCAAGTGTAATGACAGACCTGAATAAAATGTATTA
361 ---------+---------+---------+---------+---------+---------+ 420
    End
     *

AGCAGC
421 ------ 426
```

FIG. 1

```
              10        20        30        40        50
     MGGCSTRGKRPSALSLLLLLLLLSGIAASALPLESGPTGQDS--VQDATGGRRTG
      | : :|||||||  :::|::|||||:||||:||   :|:|:|  |:::
         MPLSPGLLLLLLSGATATAALPLEGGPTGRDSEHMQEAAGIRKSS 60        70        80        90       100       110
     LLTFLAWWHEWASQDSSSTAFEGGTPELSKRQERPPLQQPPHRDKKPCKNFFWKTFSSCK
     ||||||||  ||:||:|:::  ::::::|:::|||  :|  ||:::||::||:|||||||||||
     LLTFLAWWFEWTSQASAGPLIGEEAREVARRQEGAPPQQSARRDRMPCRNFFWKTFSSCK
```

FIG. 2

```
  1 QEGAPPQQSARRDRMPCRNFFWKTFSSCK  29
    QEGAPPQQSARRDRMPCRNFFWKTFSSCK
 77 QEGAPPQQSARRDRMPCRNFFWKTFSSCK 105
```

CORTISTATIN POLYPEPTIDES

This application claims the benefit of the filing date of provisional applications 60/033,980, filed on Dec. 31, 1996, and 60/037,386, filed on Feb. 7, 1997, which are herein incorporated by reference.

BACKGROUND OF THE INVENTION

1. Field of the Invention

The present invention relates to novel cortistatin polypeptides, and to polynucleotides encoding these polypeptides. More specifically, isolated nucleic acid molecules are provided encoding a Human Cortistatin polypeptide. Cortistatin polypeptides are also provided, as are vectors, host cells and recombinant methods for producing the same. Also provided are diagnostic methods for detecting variations in Human Cortistatin gene expression and therapeutic methods for treating individuals in need of an increased level of Human Cortistatin activity.

2. Related Art

The 1970's saw the initiation of a great amount of scientific discovery and research into the regulation of hormone release, especially by neuropeptides. Somatostatin, a 14 mer cyclic polypeptide was one of these neuropeptide hormone regulators. It was discovered to be released primarily in the hypothalamus, and to inhibit Growth Hormone (GH) secretion from the pituitary gland, and to decrease the GH response to secretagogues. Somatostatin is also found throughout the brain and serves as a neurotransmitter in many areas, including the spinal cord, brain stem, and cerebral cortex. It is also present in the gastrointestinal tract, where the D cells of the pancreatic islets regulate insulin and glucagon secretion.

There has been a lot of interest in studying the actions of somatostatin and analogues for efficacy in the therapy of acromegaly, secretory pancreatic tumors, pancreatitis, acute gastric ulcers and stress gastritis.

Thus, there is a continuing need in the art for isolating novel hormone-regulating peptides, especially neuropeptides of human origin, useful for therapy in various hormone mediated processes.

SUMMARY OF THE INVENTION

The present invention provides isolated nucleic acid molecules comprising a polynucleotide encoding the Human Cortistatin polypeptide having the amino acid sequence shown in FIG. 1 (amino acid residues −19 to 86 in SEQ ID NO:2) or the amino acid sequence encoded by the cDNA clone deposited as ATCC Deposit Number 97639 on Jun. 27, 1996. The nucleotide sequence determined by sequencing the deposited Cortistatin clone, which is shown in SEQ ID NO:1, contains an open reading frame encoding a polypeptide of 105 amino acid residues, including an initiation codon at positions 46–48 in SEQ ID NO:1, with a leader sequence of about 19 amino acid residues, and a predicted molecular weight of about 12 kDa. The amino acid sequence of the mature Cortistatin protein is shown in FIG. 1 (amino acid residues from about 1 to about 86 in SEQ ID NO:2).

Thus, one aspect of the invention provides an isolated nucleic acid molecule comprising a polynucleotide having a nucleotide sequence selected from the group consisting of: (a) a nucleotide sequence encoding the Human Cortistatin polypeptide having the complete amino acid sequence in SEQ ID NO:2; (b) a nucleotide sequence encoding the Human Cortistatin polypeptide having the amino acid sequence at positions from about −18 to about 86 in SEQ ID NO:2; (c) a nucleotide sequence encoding the mature Human Cortistatin polypeptide having the amino acid sequence at positions from about 1 to about 86 in SEQ ID NO:2; (d) a nucleotide sequence encoding the polypeptide having the amino acid sequence at positions from about 58 to about 86 in SEQ ID NO:2; (e) a nucleotide sequence encoding the Human Cortistatin polypeptide having the complete amino acid sequence encoded by the cDNA clone contained in ATCC Deposit No. 97639; (f) a nucleotide sequence encoding the mature Human Cortistatin polypeptide having the amino acid sequence encoded by the cDNA clone contained in ATCC Deposit No. 97639; and (g) a nucleotide sequence complementary to any of the nucleotide sequences in (a), (b), (c), (d), (e), or (f) above. Preferably, the nucleic acid molecule will encode the mature polypeptide in SEQ ID NO:2 or the mature polypeptide encoded by the above-described deposited cDNA.

Further embodiments of the invention include isolated nucleic acid molecules that comprise a polynucleotide having a nucleotide sequence at least 95% identical, and more preferably at least 96%, 97%, 98% or 99% identical, to any of the nucleotide sequences in (a), (b), (c), (d), (e), (f), or (g), above, or a polynucleotide which hybridizes under stringent hybridization conditions to a polynucleotide in (a), (b), (c), (d), (e), (f), or (g), above. This polynucleotide which hybridizes does not hybridize under stringent hybridization conditions to a polynucleotide having a nucleotide sequence consisting of only A residues or of only T residues.

An additional nucleic acid embodiment of the invention relates to an isolated nucleic acid molecule comprising a polynucleotide which encodes the amino acid sequence of an epitope-bearing portion of a Human Cortistatin polypeptide having an amino acid sequence in (a), (b), (c), (d), (e), (f), or (g), above.

The present invention also relates to recombinant vectors, which include the isolated nucleic acid molecules of the present invention, and to host cells containing the recombinant vectors, as well as to methods of making such vectors and host cells and for using them for production of Cortistatin polypeptides or peptides by recombinant techniques.

The invention further provides an isolated Human Cortistatin polypeptide having an amino acid sequence selected from the group consisting of: (a) the amino acid sequence of the Human Cortistatin polypeptide having the complete 105 amino acid sequence, including the leader sequence shown in SEQ ID NO:2; (b) the amino acid sequence of the Human Cortistatin polypeptide lacking the N-terminal methionine residue having the amino acid sequence at positions from about −18 to about 86 in SEQ ID NO:2; (c) the amino acid sequence of the mature Human Cortistatin polypeptide (without the leader) having the amino acid sequence at positions from about 1 to about 86 SEQ ID NO:2; (d) the amino acid sequence of the polypeptide having the amino acid sequence at positions from about 58 to about 86 SEQ ID NO:2; (e) the amino acid sequence of the Human Cortistatin polypeptide having the complete amino acid sequence, including the leader, encoded by the cDNA clone contained in ATCC Deposit No. 97639; and (f) the amino acid sequence of the mature Cortistatin polypeptide having the amino acid sequence encoded by the cDNA clone contained in ATCC Deposit No. 97639.

An additional embodiment of this aspect of the invention relates to a peptide or polypeptide which has the amino acid sequence of an epitope-bearing portion of a Cortistatin polypeptide having an amino acid sequence described in (a), (b), (c), (d), (e), or (f), above. Peptides or polypeptides having the amino acid sequence of an epitope-bearing portion of a Cortistatin polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a Cortistatin polypeptide having an amino acid sequence described in (a), (b), (c), (d), (e), or (f) above.

The invention further provides methods for isolating antibodies that bind specifically to a Cortistatin polypeptide having an amino acid sequence as described herein.

The present inventors have discovered that Cortistatin is expressed primarily in the brain, especially in the putamen. For a number of disorders, significantly higher or lower levels of Cortistatin gene expression can be detected in brain, especially putamen, tissue or bodily fluids (e.g., serum, plasma, urine, synovial fluid or spinal fluid) taken from an individual having such a disorder, relative to a "standard" Cortistatin gene expression level, i.e., the Cortistatin expression level in brain tissue or bodily fluids from an individual not having the disorder. Thus, the invention provides a diagnostic method useful during diagnosis of a neurological disorder, which involves (a) assaying Cortistatin gene expression level in cells or body fluid of that individual; (b) comparing that Cortistatin gene expression level with a standard Cortistatin gene expression level, whereby an increase or decrease in the assayed Cortistatin gene expression level compared to the standard expression level is indicative of said neurological disorder.

An additional aspect of the invention is related to a method for treatment of an individual in need of an increased level of Cortistatin activity in the body comprising administering to such an individual a composition comprising an isolated Cortistatin polypeptide of the invention.

BRIEF DESCRIPTION OF THE FIGURES

FIG. 1 shows the nucleotide (SEQ ID NO:1) and deduced amino acid (SEQ ID NO:2) sequences of the complete Human Cortistatin protein determined by sequencing of the HEBCI67X DNA clone contained in ATCC Deposit No. 97639. The protein has a leader sequence of about 19 amino acid residues (underlined) and a deduced molecular weight of about 12 kDa. The amino acid sequence of the predicted mature Human Cortistatin protein is shown in FIG. 1 (last 86 amino acids) and in SEQ ID NO:2 (amino acid residues from about 1 to about 86).

Figure 3:
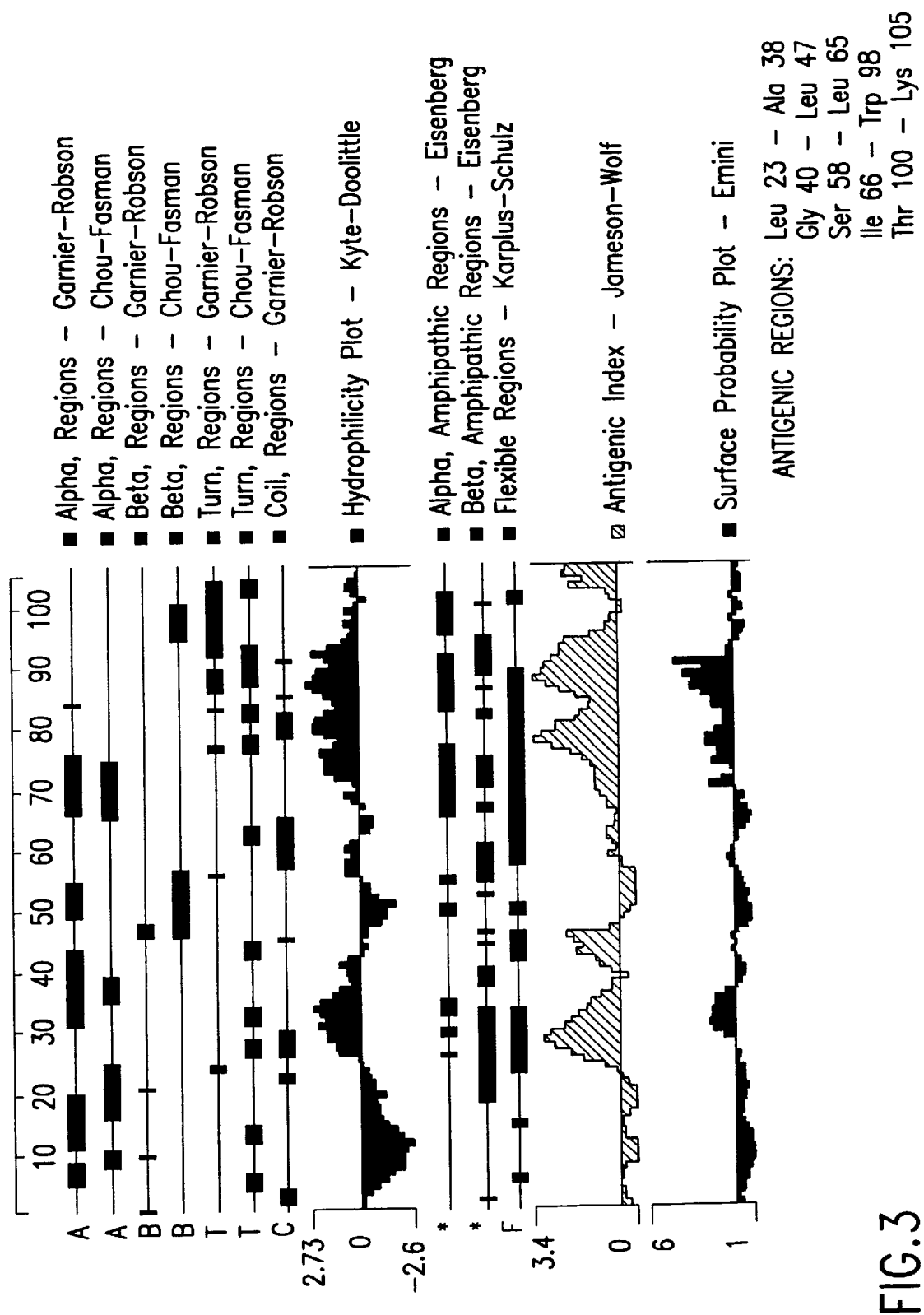

The nucleotide at position 314 in FIG. 1 (SEQ ID NO:1) may be either an A or a G resulting in the encoded amino acid being either K (lysine) or R (arginine). Similarly, the nucleotide at position 342 in FIG. 1 (SEQ ID NO:1) may be an A or a G (conserved change), and the nucleotide at position 348 in FIG. 1 (SEQ ID NO:1) may be a T or a C (conserved change).

FIG. 2 shows the regions of similarity between the amino acid sequences of the Human Cortistatin protein (lower line) and the rat Cortistatin (upper line) (SEQ ID NO:3). The sequence of the rat cortistatin is from de Lecea et al., *Nature* 381:242 (May 16, 1996).

FIG. 3 shows an analysis of the Human Cortistatin amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 23 to 38, 40 to 47, 58 to 65, 66 to 98 and 100 to 105 in FIG. 1 (amino acid residues 4 to 19, 21 to 28, 39 to 46, 47 to 79 and 81 to 86 in SEQ ID NO:2) correspond to the shown highly antigenic regions of the Human Cortistatin protein.

FIG. 4 (SEQ ID NO:4) shows the sequence of a 29 amino acid synthetic carboxy terminal peptide (upper line) spanning active fragment of mature Human Cortistatin (lower line). The sequence of this 29 amino acid fragment corresponds to amino acids 58 to 86 in SEQ ID NO:2.

DETAILED DESCRIPTION

The present invention provides isolated nucleic acid molecules comprising a polynucleotide encoding the Human Cortistatin protein having the amino acid sequence shown in SEQ ID NO:2, which was determined by sequencing a cloned cDNA. Human Cortistatin is a novel member of the brain neuropeptides. The Human Cortistatin protein of the present invention shares sequence homology with the rat cortistatin (FIG. 2) (SEQ ID NO:3), which in turn has sequence homology with somatostatin. The nucleotide sequence shown in SEQ ID NO:1 was obtained by sequencing the HEBCI67X clone, which was deposited on Jun. 27, 1996 at the American Type Culture Collection, 10801 University Blvd., Manassas, Va. 20110-2209, USA, and given accession number 97639. The deposited clone is contained in the pBluescript SK(–) plasmid (Stratagene, LaJolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in FIG. 1 (SEQ ID NO:1), a nucleic acid molecule of the present invention encoding a Cortistatin polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from human cerebellum. The determined nucleotide sequence of the Human Cortistatin cDNA of SEQ ID NO:1 contains an open reading frame encoding a protein of 105 amino acid residues with an initiation codon at positions 46–48 of the nucleotide sequence shown in SEQ ID NO:1, and a predicted leader sequence of about 19 amino acid residues, and a deduced molecular weight of about 12 kDa. The amino acid sequence of the predicted mature Human Cortistatin protein is shown in SEQ ID NO:2 amino acid residues from about 1 to about 86. The Human Cortistatin protein shown in SEQ ID NO:2 is about 56% identical and about 90% similar to rat Cortistatin (FIG. 2). As one of ordinary skill would appreciate, due to the possibilities of sequencing errors discussed above, as well as the variability of cleavage sites for leaders in different known proteins, the actual Human Cortistatin polypeptide encoded by the deposited cDNA comprises about 105 amino acids, but may be anywhere in the range of 100–110 amino acids; and the actual leader sequence of this protein is about 19 amino acids, but may be anywhere in the range of about 15 to about 25 amino acids.

As indicated, the present invention also provides the mature form(s) of the Human Cortistatin protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature Human Cortistatin polypeptides having the amino acid sequence encoded by the cDNA clone contained in ATCC Deposit No. 97639 and as shown in SEQ ID NO:2. By the mature Human Cortistatin protein having the amino acid sequence encoded by the cDNA clone contained in ATCC Deposit No. 97639 is meant the mature form(s) of the Human Cortistatin protein produced by expression in a mammalian cell (e.g., COS cells, as described below) of the complete open reading frame encoded by the human DNA sequence of the clone contained in ATCC Deposit No. 97639. As indicated below, the mature Human Cortistatin having the amino acid sequence encoded by the cDNA clone contained in ATCC Deposit No. 97639 may or may not differ from the predicted "mature" Human Cortistatin protein shown in SEQ ID NO:2 (amino acid residues from about 1 to about 86) depending on the accuracy of the predicted cleavage site based on computer analysis.

Methods for predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues –13 to +2 where +1 indicates the amino acid terminus of the mature protein. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete Cortistatin polypeptides of the present invention were analyzed by a computer program ("PSORT"). This program is available from Dr. Kenta Nakai of the Institute for Chemical Research, Kyoto University (see K. Nakai and M. Kanehisa, *Genomics* 14:897–911 (1992)). It is an expert system for predicting the cellular location of a protein based on the amino acid sequence. As part of this computational prediction of localization, the methods of McGeoch and von Heinje are incorporated. The analysis by the PSORT program predicted the cleavage sites between amino acids –1 and 1 in SEQ ID NO:2. Thereafter, the complete amino acid sequences were further analyzed by visual inspection, applying a simple form of the (–1,–3) rule of von Heine. von Heinje, supra. Thus, the leader sequence for the Cortistatin protein is predicted to consist of amino acid residues from about –19 to about –1 in SEQ ID NO:2, while the predicted mature Cortistatin protein consists of residues from about 1 to about 86.

As one of ordinary skill would appreciate, due to the possibilities of sequencing errors, as well as the variability of cleavage sites for leaders in different known proteins, the actual Cortistatin polypeptide encoded by the deposited cDNA comprises about 105 amino acids, but may be anywhere in the range of 100 to 110 amino acids; and the actual leader sequence of this protein is about 19 amino acids, but may be anywhere in the range of about 15 to about 25 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

In addition, the invention provides nucleic acid molecules having nucleotide sequences related to an extensive portion of SEQ ID NO:1. These cDNA clones are designated HEBCI67R (SEQ ID NO:9) and HSVCB08RA (SEQ ID NO:10).

The sequence of a public EST, having GenBank Accession No. W79063, related to a portion of SEQ ID NO:1 is shown in SEQ ID NO:11. This public EST is 456 nucleotides in length and contains a region of 373 nucleotides having a complementary sequence identical to nucleotides 1 to 373 of the sequence shown in SEQ ID NO:1 with the exception of seven mismatched nucleotides at positions 128, 161, 173, 306, 343, 345, and 400 in SEQ ID NO:11 and two undisclosed nucleotides at positions 163 and 412 in SEQ ID NO:11. The undisclosed nucleotides in SEQ ID NO:11 are represented by the letter "N".

In another aspect, the invention provides isolated nucleic acid molecules encoding the Human Cortistatin polypeptide having an amino acid sequence as encoded by the cDNA clone contained in the plasmid deposited as ATCC Deposit No. 97639 on Jun. 27, 1996. In a further embodiment, nucleic acid molecules are provided encoding the mature Human Cortistatin polypeptide or the full-length Human Cortistatin polypeptide lacking the N-terminal methionine. The invention also provides an isolated nucleic acid molecule having the nucleotide sequence shown in SEQ ID NO:1 or the nucleotide sequence of the Human Cortistatin cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the Human Cortistatin gene in human tissue, for instance, by Northern blot analysis. As described in detail below, detecting altered Human Cortistatin gene expression in certain tissues or bodily fluids is indicative of disorder(s) involving the hippocampus and cerebral cortex regions of the brain.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course larger DNA fragments 50, 100, 150, 200, 250, 300, 350, 400, or 425 nt in length of the sequence shown in SEQ ID NO:1 are also useful according to the present invention as are fragments corresponding to most, if not all, of the nucleotide sequence of the cDNA clone contained in the plasmid deposited as ATCC Deposit No. 97639 or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1. Since the gene has been deposited and the nucleotide sequence shown in SEQ ID NO:1 is provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of the Human Cortistatin protein. In particular, such nucleic acid fragments of the present invention include nucleic acid molecules encoding: a polypeptide comprising amino acid residues from about 4 to about 19 in SEQ ID NO:2; a polypeptide comprising amino acid residues from about 21 to about 28 in SEQ ID NO:2; a polypeptide comprising amino acid residues from about 39 to about 46 in SEQ ID NO:2; a polypeptide comprising amino acid residues from about 47 to about 79 in SEQ ID NO:2; and a polypeptide comprising amino acid residues from about 81 to about 86 in SEQ ID NO:2. The inventors have determined that the above polypeptide fragments are antigenic regions of the Human Cortistatin protein. Methods for determining other such epitope-bearing portions of the Human Cortistatin protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 97639. By "stringent hybridization conditions" is intended overnight incubation at 42° C. in a solution comprising: 50% formamide, 5×SSC ((750mM NaCl, 75 mM) trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50–300 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in SEQ ID NO:1. By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual*, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a Human Cortistatin cDNA clone has been deposited and its determined nucleotide sequence is provided in SEQ ID NO:1, generating polynucleotides which hybridize to a portion of the Human Cortistatin cDNA molecule would be routine to the skilled artisan. For example, restriction endonuclease cleavage or shearing by sonication of the Human Cortistatin cDNA clone could easily be used to generate DNA portions of various sizes which are polynucleotides that hybridize to a portion of the Human Cortistatin cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the Human Cortistatin cDNA shown in SEQ ID NO:1), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode the Cortistatin protein may include, but are not limited to those encoding the amino acid sequence of the mature polypeptide, by itself; the coding sequence for the mature polypeptide and additional sequences, such as those encoding the about 19 amino acid leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767 (1984). As discussed below, other such fusion proteins include Human Cortistatin fused to Fc at the N- or C-terminus.

The present invention further relates to variants of the nucleic acid molecules of the present invention, which encode portions, analogs or derivatives of the Cortistatin protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the Cortistatin protein or portions thereof. Also especially preferred in this regard are conservative substitutions. Most highly preferred are nucleic acid molecules encoding the mature protein having the amino acid sequence shown in SEQ ID NO:2 or the mature Human Cortistatin amino acid sequence encoded by the deposited cDNA clone.

The nucleotide at position 314 in FIG. 1 (SEQ ID NO:1) may be either an A or a G resulting in the encoded amino acid being either K (lysine) or R (arginine). Similarly, position 342 may be an A or a G (conserved change), and position 348 may be a T or a C (conserved change).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 86 in SEQ ID NO:2; (d) a nucleotide sequence encoding the polypeptide having the amino acid sequence at positions from about 58 to about 86 in SEQ ID NO:2; (e) a nucleotide sequence encoding the polypeptide having the amino acid sequence encoded by the cDNA clone contained in ATCC Deposit No. 97639; (f) a nucleotide sequence encoding the mature Human Cortistatin polypeptide having the amino acid sequence encoded by the cDNA clone contained in ATCC Deposit No. 97639; or (g) a nucleotide sequence complementary to any of the nucleotide sequences in (a), (b), (c), (d), (e), or (f).

By a polynucleotide having a nucleotide sequence at least, for example, 95% "identical" to a reference nucleotide sequence encoding a Human Cortistatin polypeptide is intended that the nucleotide sequence of the polynucleotide is identical to the reference sequence except that the polynucleotide sequence may include up to five point mutations per each 100 nucleotides of the reference nucleotide sequence encoding the Human Cortistatin polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO:1 or to the nucleic acid sequence of the deposited cDNA, irrespective of whether they encode a polypeptide having Cortistatin activity. This is because even where a particular nucleic acid molecule does not encode a polypeptide having Cortistatin activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Cortistatin activity include, inter alia, (1) isolating the Cortistatin gene or allelic variants thereof in a cDNA library; (2) in situ hybridization (e.g., "FISH") to metaphase chromosomal spreads to provide precise chromosomal location of the Cortistatin gene, as described in Verma et al., *Human Chromosomes: A Manual of Basic Techniques*, Pergamon Press, New York (1988); and (3) Northern Blot analysis for detecting Cortistatin mRNA expression in specific tissues (e.g., putamen, cerebral cortex and hippocampus).

Preferred, however, are nucleic acid molecules having sequences at least 95%, 96%, 97%, 98% or 99% identical to the nucleic acid sequence shown in SEQ ID NO:1 or to the nucleic acid sequence of the deposited cDNA which do, in fact, encode a polypeptide having Cortistatin protein activity. By "a polypeptide having Cortistatin activity" is intended polypeptides exhibiting activity similar, but not necessarily identical, to an activity of the Cortistatin protein of the invention (either the full-length protein or, preferably, the mature protein), as measured in a particular biological assay.

Human Cortistatin exhibits activity in sleep regulation, for example, by depressing neuronal electrical activity, inducing low frequency cerebral waves in the cerebral cortex, and antagonizing the effects of acetylcholine in the hippocampus and cortex measures of excitability. For example, one can measure Cortistatin activity by manually depolarizing a CA1 neuron to about −65 mV (resting potential at about −70 mV) to elicit action potential firing. Superfusion by 1 μM Human Cortistatin would abolish the action potential discharge. One can measure Population Spike (PS) amplitudes in CA1 neurons in vivo, by generating stimulus response curves and relating the PS amplitude monotonically to stimulus intensity tested at three response levels: threshold, half-maximal, and maximal. Microiontophoretic applications of 1 mg ml$^{-1}$ of Cortistatin or a polypeptide having Cortistatin activity would significantly decrease PS amplitudes in CA1. Another assay for polypeptides having Cortistatin activity is the effect of intracerebroventricular administration to male Sprague—Dawley rats, anesthetized with halothane, of the polypeptide in question on the sleep-wake cycle of the rat. An active polypeptide would increase the period of slow wave sleep and decrease REM sleep. Yet another assay is the inhibition effect by the Cortistatin activity-exhibiting polypeptide on local Electroencephalographic Activity (EEG) in the visual cortex which would otherwise be seen by administration of acetyl choline (ACh). Microiontophoretic application of Cortistatin and ACh, or of Cortistatin alone will not increase the averaged EEG power spectra in the 8–16 Hz frequency range, whereas administration of ACh alone will markedly increase such power spectra.

Thus, "a polypeptide having Cortistatin protein activity" includes polypeptides that also exhibit any of the same neuropeptide modulating activities in the above-described assays in a dose-dependent manner. Although the degree of dose-dependent activity need not be identical to that of the Human Cortistatin protein, preferably, "a polypeptide having Cortistatin protein activity" will exhibit substantially similar dose-dependence in a given activity as compared to the Cortistatin protein (i.e., the candidate polypeptide will exhibit greater activity or not more than about tenfold less and, preferably, not more than about twofold less activity relative to the reference Human Cortistatin protein). One polypeptide believed to have Cortistatin protein activity is the 29 amino acid sequence shown in FIG. 4 (SEQ ID NO:4) (amino acids from about 58 to about 86 in SEQ ID NO:2).

Of course, due to the degeneracy of the genetic code, one of ordinary skill in the art will immediately recognize that a large number of the nucleic acid molecules having a sequence at least 95%, 97%, 98%, or 99% identical to the nucleic acid sequence of the deposited cDNA or the nucleic acid sequence shown in SEQ ID NO:1 will encode "a polypeptide having Cortistatin protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Cortistatin protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U., et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., supra, and the references cited therein.

Vectors and Host Cells

The present invention also relates to vectors which include the isolated DNA molecules of the present invention, host cells which are genetically engineered with the recombinant vectors, and the production of Cortistatin polypeptides or fragments thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EPO 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EPO 232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The Cortistatin protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Cortistatin Polypeptides and Fragments

The invention further provides an isolated Cortistatin polypeptide having the amino acid sequence encoded by the deposited cDNA, or the amino acid sequence in SEQ ID NO:2, or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the Cortistatin polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the Cortistatin polypeptide which show substantial Cortistatin polypeptide activity or which include regions of Cortistatin protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the Cortistatin protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Trypiophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above and below. Generally speaking, the number of substitutions for any given Cortistatin polypeptide, or mutant thereof, will not be more than 50, 40, 30, 20, 10, 5, or 3, depending on the objective.

Amino acids in the Cortistatin protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity using the assays described supra. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the Human Cortistatin polypeptide can be substantially purified by the one-step method described in Smith and Johnson, Gene 67:31–40 (1988).

The polypeptides of the present invention are preferably provided in an isolated form, and preferably are substantially purified. A recombinantly produced version of the Cortistatin polypeptide can be substantially purified by the one-step method described in Smith and Johnson, Gene 67:31–40 (1988).

The polypeptides of the present invention include the polypeptide encoded by the deposited cDNA including the leader, the mature polypeptide encoded by the deposited the cDNA minus the leader (i.e., the mature protein), a polypeptide comprising amino acids about −19 to about 86 in SEQ ID NO:2; a polypeptide comprising amino acids about −18 to about 86 in SEQ ID NO:2; a polypeptide comprising amino acids about 1 to about 86 in SEQ ID NO:2; a polypeptide comprising amino acids about 58 to about 86 in SEQ ID NO:2; as well as polypeptides which are at least 95% identical, more preferably at least 96% or 97% identical, still more preferably at least 98% or 99% identical to those described above and also include portions of such polypeptides with at least 30 amino acids and more preferably at least 50 amino acids.

By a polypeptide having an amino acid sequence at least, for example, 95% "identical" to a reference amino acid sequence of a Human Cortistatin polypeptide is intended that the amino acid sequence of the polypeptide is identical to the reference sequence except that the polypeptide sequence may include up to five amino acid alterations per each 100 amino acids of the reference amino acid of the Human Cortistatin polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 or to the amino acid sequence encoded by the deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting Cortistatin protein expression as described below or as agonists and antagonists capable of enhancing or inhibiting Cortistatin protein function. Further, such polypeptides can be used in the yeast two-hybrid system to "capture" Cortistatin protein binding proteins which are also candidate agonist and antagonist according to the present invention. The yeast two hybrid system is described in Fields and Song, Nature 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., Cell 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate Cortistatin-specific antibodies include: a polypeptide comprising amino acid residues from about 4 to about 19 in SEQ ID NO:2; a polypeptide comprising amino acid residues from about 21 to about 28 in SEQ ID NO:2; a polypeptide comprising amino acid residues from about 39 to about 46 in SEQ ID NO:2; a polypeptide comprising amino acid residues from about 47 to about 79 in SEQ ID NO:2; and a polypeptide comprising amino acid residues from about 81 to about 86 in SEQ ID NO:2. As indicated above, the inventors have determined that the above polypeptide fragments are antigenic regions of the Cortistatin protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 $\mu$g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, Cortistatin polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo This has been shown, e.g., for chimeric proteins consisting of the first two domains of the human CD4-polypeptide and various domains of the constant regions of the heavy or light chains of mammalian immunoglobulins (EP 394 827; Traunecker et al., *Nature* 331:84–86 (1988)). Fusion proteins that have a disulfide-linked dimeric structure due to the IgG part can also be more efficient in binding and neutralizing other molecules than the monomeric Cortistatin protein or protein fragment alone (Fountoulakis et al., *J. Biochem*. 270:3958–3964 (1995)).

Neurological Disorder Diagnosis

Cortistatin is expressed primarily in the putamen. For a number of neurological, sleep-related disorders, substantially altered (increased or decreased) levels of Cortistatin gene expression can be detected in brain tissue or other cells or bodily fluids (e.g., sera, plasma, urine, synovial fluid or spinal fluid) taken from an individual having such a disorder, relative to a "standard" Cortistatin gene expression level, that is, the Cortistatin expression level in tissue or bodily fluids from an individual not having the disorder. Thus, the invention provides a diagnostic method useful during diagnosis of a sleep disorder, which involves measuring the expression level of the gene encoding the Cortistatin protein in brain tissue or other cells or body fluid from an individual and comparing the measured gene expression level with a standard Cortistatin gene expression level, whereby an increase or decrease in the gene expression level compared to the standard is indicative of such a disorder.

By individual is intended mammalian individuals, preferably humans. By "measuring the expression level of the gene encoding the Cortistatin protein" is intended qualitatively or quantitatively measuring or estimating the level of the Cortistatin protein or the level of the mRNA encoding the Cortistatin protein in a first biological sample either directly (e.g., by determining or estimating absolute protein level or mRNA level) or relatively (e.g., by comparing to the Cortistatin protein level or mRNA level in a second biological sample). Preferably, the Cortistatin protein level or mRNA level in the first biological sample is measured or estimated and compared to a standard Cortistatin protein level or mRNA level, the standard being taken from a second biological sample obtained from an individual not having the disorder or being determined by averaging levels from a population of individuals not having a neurological sleep disorder. As will be appreciated in the art, once a standard Cortistatin protein level or mRNA level is known, it can be used repeatedly as a standard for comparison.

By "biological sample" is intended any biological sample obtained from an individual, body fluid, cell line, tissue culture, or other source which contains Cortistatin protein or mRNA. As indicated, biological samples include body fluids (such as sera, plasma, urine, synovial fluid and spinal fluid) which contain secreted mature Cortistatin protein, brain tissue, and other tissue sources found to express Cortistatin or a Cortistatin receptor. Methods for obtaining tissue biopsies and body fluids from mammals are well known in the art. Where the biological sample is to include mRNA, a tissue biopsy is the preferred source.

The present invention is useful for diagnosis or treatment of various neurological-related disorders in mammals, preferably humans. Such disorders include the following tumors and cancers, hypoactivity, hyperactivity, atrophy, enlargement of the putamen, and the like.

Total cellular RNA can be isolated from a biological sample using any suitable technique such as the single-step guanidinium-thiocyanate-phenol-chloroform method described in Chomczynski and Sacchi, *Anal. Biochem*. 162:156–159 (1987). Levels of mRNA encoding the Cortistatin protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Cortistatin protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably be at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the Cortistatin protein). Northern blot analysis can be performed as described above.

Preferably, levels of mRNA encoding the Cortistatin protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the Human Cortistatin protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying Cortistatin protein levels in a biological sample can occur using any art-known method. Preferred for assaying Cortistatin protein levels in a biological sample are antibody-based techniques. For example, Cortistatin protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of Cortistatin protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of Cortistatin protein can be accomplished using isolated Cortistatin protein as a standard. This technique can also be applied to body fluids. With these samples, a molar concentration of Cortistatin protein will aid to set standard values of Cortistatin protein content for different body fluids, like serum, plasma, urine, synovial fluid, spinal fluid, etc. The normal appearance of Cortistatin protein amounts can then be set using values from healthy individuals, which can be compared to those obtained from a test subject.

Other antibody-based methods useful for detecting Cortistatin protein levels include immunoassays, such as the enzyme linked immunosorbent assay (ELISA) and the radio-immunoassay (RIA). For example, Human Cortistatin protein-specific monoclonal antibodies can be used both as an immunoadsorbent and as an enzyme-labeled probe to detect and quantify the Cortistatin protein. The amount of Cortistatin protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect Cortistatin protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting Cortistatin protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying Cortistatin protein levels in a biological sample obtained from an individual, Cortistatin protein can also be detected in vivo by imaging. Antibody labels or markers for in vivo imaging of Cortistatin protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A Cortistatin protein-specific antibody or antibody portion which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for a disorder involving the hippocampus and/or the cerebral cortex regions of the brain. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99m}$Tc. The labeled antibody or antibody portion will then preferentially accumulate at the location of cells which contain Cortistatin protein. In vivo tumor imaging is described in S. W. Burchiel et al., "Immunopharmacokinetics of Radiolabeled Antibodies and Their Portions" (Chapter 13 in *Tumor Imaging: The Radiochemical Detection of Cancer*, eds., S. W. Burchiel and B. A. Rhodes, Masson Publishing Inc. (1982)).

Cortistatin-protein specific antibodies for use in the present invention can be raised against the intact Cortistatin protein or an antigenic polypeptide portion thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody portions (such as, for example, Fab and F(ab')$_2$ portions) which are capable of specifically binding to Human Cortistatin protein. Fab and F(ab')$_2$ portions lack the Fc portion of intact antibody, clear more rapidly from the circulation, and may have less non-specific tissue binding of an intact antibody (Wahl et al., *J. Nucl. Med.* 24:316–325 (1983)). Thus, these portions are preferred.

The antibodies of the present invention may be prepared by any of a variety of methods. For example, cells expressing the Cortistatin protein or an antigenic portion thereof can be administered to an animal in order to induce the production of sera containing polyclonal antibodies. In a preferred method, a preparation of Cortistatin protein is prepared and purified as described above to render it substantially free of natural contaminants. Such a preparation is then introduced into an animal in order to produce polyclonal antisera of greater specific activity.

In the most preferred method, the antibodies of the present invention are monoclonal antibodies (or Cortistatin protein binding portions thereof). Such monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et al., In: Monoclonal Antibodies and T-Cell Hybridomas, Elsevier, N.Y., pp. 563–681 (1981)). In general, such procedures involve immunizing an animal (preferably a mouse) with a Cortistatin protein antigen or, more preferably, with a Cortistatin protein-expressing cell. Suitable cells can be recognized by their capacity to bind anti-Cortistatin protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 µg/l of nonessential amino acids, about 1,000 U/m of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Manassas, Va. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the Cortistatin antigen.

Alternatively, additional antibodies capable of binding to the Cortistatin protein antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, Cortistatin protein specific antibodies are used to immunize an animal, preferably a mouse. The splenocytes of such an animal are then used to produce hybridoma cells, and the hybridoma cells are screened to identify clones which produce an antibody whose ability to bind to the Cortistatin protein-specific antibody can be blocked by the Cortistatin protein antigen. Such antibodies comprise anti-idiotypic antibodies to the Cortistatin protein-specific antibody and can be used to immunize an animal to induce formation of further Cortistatin protein-specific antibodies.

It will be appreciated that Fab and F(ab')$_2$ and other portions of the antibodies of the present invention may be used according to the methods disclosed herein. Such portions are typically produced by proteolytic cleavage, using enzymes such as papain (to produce Fab portions) or pepsin (to produce F(ab')$_2$ portions). Alternatively, Cortistatin protein-binding portions can be produced through the application of recombinant DNA technology or through synthetic chemistry.

Where in vivo imaging is used to detect enhanced levels of Cortistatin protein for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, Science 229:1202 (1985); Oi et al., Bio Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

Additionally, it is also possible to use so called Single Chain Antibodies, which contain the variable region of a light chain, the variable region of a heavy chain, both of these variable regions fused via a peptide linker. Such antibodies are described, for example in Ladner et al. U.S. Pat. No. 4,946,778.

Any of the antibodies of the invention can be either mono or bispecific.

Further suitable labels for the Cortistatin protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, 125I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., Eur. J. Nucl. Med. 10:296–301 (1985); Carasquillo et al., J. Nucl. Med. 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861–870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al. (Clin. Chim. Acta 70:1–31 (1976)), and Schurs et al. (Clin. Chim. Acta 81:1–40 (1977)). Coupling techniques mentioned in the latter are the glutaraldehyde method, the periodate method, the dimaleimide method, and the m-maleimidobenzyl-N-hydroxy-succinimide ester method, all of which methods are incorporated by reference herein.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a Cortistatin protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Treatment of Sleep-Related and Other Neurological Disorders

It will be appreciated by one of ordinary skill that, since the Cortistatin protein of the invention is translated with a leader peptide suitable for secretion of the mature protein from the cells which express Cortistatin, when Cortistatin protein (particularly the mature form) is added from an exogenous source to cells, tissues or the body of an individual, the protein will exert its modulating activities on any of its target cells of that individual. Therefore, it will be appreciated that conditions caused by a decrease in the standard or normal level of Cortistatin activity in an individual, particularly sleep disorders, can be treated be administration of Cortistatin protein. Thus, the invention also provides a method of treatment of an individual in need of an increased level of Cortistatin activity comprising administering to such an individual a pharmaceutical composition comprising an amount of an isolated Cortistatin polypeptide of the invention, particularly a mature form of the Cortistatin protein of the invention, effective to increase the Cortistatin activity level in such an individual.

Such conditions are generally those related to regulating neuronal activity in an individual, especially sleep. The Cortistatin of the invention antagonizes the effects of ACh in both the hippocampus and the cortex, and is to administered when such effects are desired.

One of ordinary skill will appreciate that effective amounts of the Cortistatin polypeptides for treating an individual in need of an increased level of Cortistatin activity (including amounts of Cortistatin polypeptides effective for sleep regulation) can be determined empirically for each condition where administration of Cortistatin is indicated. The polypeptide having Cortistatin activity may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition and other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts.

The Cortistatin composition to be used in the therapy will be formulated and dosed in a fashion consistent with good medical practice, taking into account the clinical condition of the individual patient (especially the side effects of treatment with Cortistatin alone), the site of delivery of the Cortistatin composition, the method of administration, the scheduling of administration, and other factors known to practitioners. The "effective amount" of Cortistatin for purposes herein (including a Cortistatin effective amount) is thus determined by such considerations.

As a general proposition, the total pharmaceutically effective amount of the Cortistatin administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Cortistatin is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The key factor in selecting an appropriate dose is the result obtained, as measured by decreases in neuronal activity, sleep alterations, etc.

A course of Cortistatin treatment to affect the neurological system appears to be optimal if continued longer than a certain minimum number of days. The length of treatment needed to observe changes and the interval following treatment for responses to occur appears to vary depending on the desired effect.

The Cortistatin is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (U. Sidman et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Sustained-release Cortistatin compositions also include liposomally entrapped Cortistatin. Liposomes containing Cortistatin are prepared by methods known per se: DE 3,218,121; Epstein, et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Cortistatin therapy.

For parenteral administration, in one embodiment, the Cortistatin is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the Cortistatin uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Cortistatin is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of Cortistatin salts.

Cortistatin to be used for therapeutic administration must be sterile. Sterility is readily accomplished by filtration through sterile filtration membranes (e.g., 0.2 micron membranes). Therapeutic Cortistatin compositions generally are placed into a container having a sterile access port, for example, an intravenous solution bag or vial having a stopper pierceable by a hypodermic injection needle.

Cortistatin ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous Cortistatin solution, and the resulting mixture is lyophilized. The infusion solution is prepared by reconstituting the lyophilized Cortistatin using bacteriostatic Water-for-Injection.

The active polypeptide can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the agent or inhibitor, stabilizers, preservatives, excipients, and the like. The preferred lipids are the phospholipids and the phosphatidyl cholates (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

Having generally described the invention, the same will be more readily understood by reference to the following examples, which are provided by way of illustration and are not intended as limiting.

EXAMPLES

Example 1

Cloning and Expression of Human Cortistatin in a Baculovirus Expression System

In this illustrative example, the plasmid shuttle vector pA2 is used to insert the cloned DNA encoding the complete protein, including its naturally associated secretary signal (leader) sequence, into a baculovirus to express the mature Human Cortistatin protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the full length Human Cortistatin protein in the deposited clone, including the AUG initiation codon and the naturally associated leader sequence shown in FIG. 1 (SEQ ID NO:2), is amplified using PCR oligonucleotide primers corresponding to the 5' and 3' sequences of the gene. The 5' primer has the sequence: 5' GACT GGATCCGCCATCATGCCATTGTCCCCGGCC 3' (SEQ ID NO:5) containing the underlined BamHI restriction enzyme site, an efficient signal for initiation of translation in eukaryotic cells, as described by Kozak, M., *J. Mol. Biol.* 196:947–950 (1987), followed by 19 bases of the sequence of the complete Human Cortistatin protein shown in FIG. 1, beginning with the AUG initiation codon. The 3' primer has the sequence:
5' GACTGGTACCGGTCTGTCATTACACTTGC 3' (SEQ ID NO:6) containing the underlined, Asp718 restriction site followed by 17 nucleotides complementary to the 3' noncoding sequence in FIG. 1.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein "F1".

The plasmid is digested with the restriction enzymes BamHI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the Human Cortistatin gene using the PCR method, in which one of the primers that is used to amplify the gene and the second primer is from well within the vector so that only those bacterial colonies containing the Human Cortistatin gene fragment will show amplification of the DNA. The sequence of the cloned fragment is confirmed by DNA sequencing. This plasmid is designated herein pBacCortistatin.

Five μg of the plasmid pBacCortistatin is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 μg of BaculoGold™ virus DNA and 5 μg of the plasmid pBacCortistatin are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-Cortistatin.

To verify the expression of the Human Cortistatin gene, Sf9 cells are grown in Grace's medium supplemented with 10% heat inactivated FBS. The cells are infected with the recombinant baculovirus V-Cortistatin at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 2

Expression and Purification of Human Cortistatin in *E. coli*

The bacterial expression vector pQE60 is used for bacterial expression in this example (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6 X His tag") covalently linked to the carboxyl terminus of that polypeptide. However, in this example, the polypeptide coding sequence is inserted such that translation of the six His codons is prevented and, therefore, the polypeptide is produced with no 6 X His tag.

The DNA sequence encoding the desired portion of the Human Cortistatin protein lacking the hydrophobic leader sequence is amplified from the deposited cDNA clone using PCR oligonucleotide primers which anneal to the amino terminal sequences of the desired portion of the Human Cortistatin protein and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5' primer has the sequence:

5' GACTCCATGGCCCTGCCCCTGGAGG 3' (SEQ ID NO:7) containing the underlined NcoI restriction site followed by 15 nucleotides complementary to the amino terminal coding sequence of the mature Human Cortistatin sequence in FIG. 1. One of ordinary skill in the art would appreciate, of course, that the point in the protein coding sequence where the 5' primer begins may be varied to amplify a desired portion of the complete protein shorter or longer than the mature form. The 3' primer has the sequence:

5' AGATCTTTTGCAGGAGGAGAAGG 3' (SEQ ID NO:8) containing the underlined BglII restriction site followed by 17 nucleotides complementary to the 3' end of the protein coding sequence in the Human Cortistatin DNA sequence in FIG. 1.

The amplified Human Cortistatin DNA fragments and the vector pQE60 are digested with NcoI and BglII and the digested DNAs are then ligated together. Insertion of the Human Cortistatin DNA into the restricted pQE60 vector places the Human Cortistatin protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing Human Cortistatin protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the Human Cortistatin is dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure Human Cortistatin protein. The purified protein is stored at 4° C. or frozen at −80° C.

Example 3

Cloning and Expression of Human Cortistatin in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human HeLa 293, H9 and Jurkat cells, mouse NIH3T3 and C127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pCortistatin HA, is made by cloning a cDNA encoding Human Cortistatin into the expression vector pcDNAI/Amp or pcDNAIII (which can be obtained from Invitrogen, Inc.).

The expression vector pcDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., Cell 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the Human Cortistatin protein is cloned into the polylinker region of the vector so that recombinant protein expression is directed by the CMV promoter. The plasmid construction strategy is as follows. The Human Cortistatin cDNA of the deposited clone is amplified using primers that contain convenient restriction sites, much as described above for construction of vectors for expression of Human Cortistatin in E. coli. Suitable primers include the following, which are used in this example. The 5' primer, containing the underlined BamHI site, a Kozak sequence, an AUG start codon and 19 nucleotides of the 5' coding region of the complete Human Cortistatin coding sequence has the following sequence:

5' GACT GGATCCGCCATCATGCCATTGTCCCCGGCC 3' (SEQ ID NO:5).

The 3' primer, containing the underlined Asp718 site, a stop codon, and 17 bp of 3' non-coding sequence has the following sequence:

5' GACTGGTACCGGTCTGTCATTACACTTGC 3' (SEQ ID NO:6).

The PCR amplified DNA fragment and the vector, pcDNAI/Amp, are digested with BamHI and Asp718 and then ligated. The ligation mixture is transformed into E. coli strain SURE (available from Stratagene Cloning Systems, 11099 North Torrey Pines Road, La Jolla, Calif. 92037), and the—transformed culture is plated on ampicillin media plates which then are incubated to allow growth of ampicillin resistant colonies. Plasmid DNA is isolated from resistant colonies and examined by restriction analysis or other means for the presence of the Human Cortistatin-encoding fragment.

For expression of recombinant Human Cortistatin, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of Human Cortistatin by the vector.

Expression of the Human Cortistatin-HA fusion protein is detected by radiolabeling and immunoprecipitation, using methods described in, for example Harlow et al., Antibodies: A Laboratory Manual, 2nd Ed., Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of Human Cortistatin protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molecular and Cellular Biology, March 1985:438–447) plus a fragment isolated from the enhancer of the immediate early gene of human cytomegalovirus (CMV) (Boshart et al., Cell 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the Human Cortistatin in a regulated way in mammalian cells (Gossen, M., & Bujard, H. 1992, Proc. Natl. Acad. Sci. USA 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphatase by procedures known in the art. The vector is then isolated from a 1% agarose gel.

The DNA sequence encoding the complete Human Cortistatin protein including its leader sequence is amplified using PCR oligonucleotide primers corresponding to the 5' and 3' sequences of the gene. The 5' primer has the sequence: 5' GACT GGATCCGCCATCATGCCATTGTCCCCGGCC 3' (SEQ ID NO:5) containing the underlined BamHI restriction enzyme site followed by an efficient signal for initiation of translation in eukaryotes, as described by Kozak, M., *J. Mol. Biol.* 196:947–950 (1987), and 19 bases of the coding sequence of Human Cortistatin shown in FIG. 1 (SEQ ID NO:1). The 3' primer has the sequence: 5' GACTGGTACCGGTCTGTCATTACACTTGC 3' (SEQ ID NO:6) containing the underlined Asp718 restriction site followed by 17 nucleotides complementary to the non-translated region of the Human Cortistatin gene shown in FIG. 1 (SEQ ID NO:1).

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 µg of the expression plasmid pC4 is cotransfected with 0.5 µg of the plasmid pSV2-neo using lipofectin (Felgner et al., supra). The plasmid pSV2 neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 µM, 20 µM). The same procedure is repeated until clones are obtained which grow at a concentration of 100–200 µM. Expression of the desired gene product is analyzed, for instance, by SDS-PAGE and Western blot or by reverse phase HPLC analysis.

Example 4

Tissue Distribution of Human Cortistatin mRNA Expression

Northern blot analysis is carried out to examine Human Cortistatin gene expression in human tissues, using methods described by, among others, Sambrook et al., cited above. A cDNA probe containing the entire nucleotide sequence of the Human Cortistatin protein (SEQ ID NO:1) is labeled with $^{32}$p using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for Human Cortistatin mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polynucleotide comprising a nucleotide sequence identical to nucleotides 241–339 of SEQ ID NO:1.

2. An isolated polynucleotide comprising a nucleotide sequence identical to nucleotides 274–360 of SEQ ID NO:1.

3. The isolated polynucleotide of claim 2, comprising a nucleotide sequence identical to nucleotides 103–360 of SEQ ID NO:1.

4. The isolated polynucleotide of claim 3, comprising a nucleotide sequence identical to nucleotides 49–360 of SEQ ID NO:1.

5. The isolated polynucleotide of claim 4, comprising a nucleotide sequence identical to nucleotides 46–360 of SEQ ID NO:1.

6. The isolated polynucleotide of claim 5, comprising the nucleotide sequence of SEQ ID NO:1.

7. An isolated polynucleotide comprising a variant of nucleotides 241–339 of SEQ ID NO:1, wherein at position 314, guanosine is replaced with adenosine.

8. An isolated polynucleotide comprising a variant of nucleotides 274–360 of SEQ ID NO:1, wherein at position 314, guanosine is replaced with adenosine.

9. The isolated polynucleotide of claim 8, comprising a variant of nucleotides 103–360 of SEQ ID NO:1, wherein at position 314, guanosine is replaced with adenosine.

10. The isolated polynucleotide of claim 9, comprising a variant of nucleotides 49–360 of SEQ ID NO:1, wherein at position 314, guanosine is replaced with adenosine.

11. The isolated polynucleotide of claim 10, comprising a variant of nucleotides 46–360 of SEQ ID NO:1, wherein at position 314, guanosine is replaced with adenosine.

12. The isolated polynucleotide of claim 11, comprising a variant of SEQ ID NO:1, wherein at position 314, guanosine is replaced with adenosine.

13. An isolated polynucleotide comprising, a variant of nucleotides 274–360 of SEQ ID NO:1, wherein at position 342, guanosine is replaced with adenosine.

14. The isolated polynucleotide of claim 13, comprising a variant of nucleotides 103–360 of SEQ ID NO:1, wherein at position 342, guanosine is replaced with adenosine.

15. The isolated polynucleotide of claim 14, comprising a variant of nucleotides 49–360 of SEQ ID NO:1, wherein at position 342, guanosine is replaced with adenosine.

16. The isolated polynucleotide of claim 15, comprising a variant of nucleotides 46–360 of SEQ ID NO:1, wherein at position 342, guanosine is replaced with adenosine.

17. The isolated polynucleotide of claim 16, comprising a variant of SEQ ID NO:1, wherein at position 342, guanosine is replaced with adenosine.

18. An isolated polynucleotide comprising a variant of nucleotides 274–360 of SEQ ID NO:1, wherein at position 348, cytidine is replaced with thymidine.

19. The isolated polynucleotide of claim 18, comprising a variant of nucleotides 103–360 of SEQ ID NO:1, wherein at position 348, cytidine is replaced with thymidine.

20. The isolated polynucleotide of claim 19, comprising a variant of nucleotides 49–360 of SEQ ID NO:1, wherein at position 348, cytidine is replaced with thymidine.

21. The isolated polynucleotide of claim 20, comprising a variant of nucleotides 46–360 of SEQ ID NO:1, wherein at position 348, cytidine is replaced with thymidine.

22. The isolated polynucleotide of claim 21, comprising a variant of SEQ ID NO:1, wherein at position 348, cytidine is replaced with thymidine.

23. An isolated polynucleotide comprising a variant of nucleotides 274–360 of SEQ ID NO:1, wherein at positions 314 and 342, guanosine is replaced with adenosine.

24. The isolated polynucleotide of claim 23, comprising a variant of nucleotides 103–360 of SEQ ID NO:1, wherein at positions 314 and 342, guanosine is replaced with adenosine.

25. The isolated polynucleotide of claim 24, comprising a variant of nucleotides 49–360 of SEQ ID NO:1, wherein at positions 314 and 342, guanosine is replaced with adenosine.

26. The isolated polynucleotide of claim 25, comprising a variant of nucleotides 46–360 of SEQ ID NO:1, wherein at positions 314 and 342, guanosine is replaced with adenosine.

27. The isolated polynucleotide of claim 26, comprising a variant of SEQ ID NO:1, wherein at positions 314 and 342, guanosine is replaced with adenosine.

28. An isolated polynucleotide comprising a polynucleotide variant of nucleotides 274–360 of SEQ ID NO:1, wherein at position 314, guanosine is replaced with adenosine and wherein at position 348, cytidine is replaced with thymidine.

29. The isolated polynucleotide of claim 28, comprising a variant of nucleotides 103–360 of SEQ ID NO:1, wherein at position 314, guanosine is replaced with adenosine and wherein at position 348, cytidine is replaced with thymidine.

30. The isolated polynucleotide of claim 29, comprising a variant of nucleotides 49–360 of SEQ ID NO:1, wherein at position 314, guanosine is replaced with adenosine and wherein at position 348, cytidine is replaced with thymidine.

31. The isolated polynucleotide of claim 30, comprising a variant of nucleotides 46–360 of SEQ ID NO:1, wherein at position 314, guanosine is replaced with adenosine and wherein at position 348, cytidine is replaced with thymidine.

32. The isolated polynucleotide of claim 31, comprising a variant of SEQ ID NO:1, wherein at position 314, guanosine is replaced with adenosine and wherein at position 348, cytidine is replaced with thymidine.

33. An isolated polynucleotide comprising a variant of nucleotides 274–360 of SEQ ID NO:1, wherein at position 342, guanosine is replaced with adenosine and wherein at position 348, cytidine is replaced with thymidine.

34. The isolated polynucleotide of claim 33, comprising a variant of nucleotides 103–360 of SEQ ID NO:1, wherein at position 342, guanosine is replaced with adenosine and wherein at position 348, cytidine is replaced with thymidine.

35. The isolated polynucleotide of claim 34, comprising a variant of nucleotides 49–360 of SEQ ID NO:1, wherein at position 342, guanosine is replaced with adenosine and wherein at position 348, cytidine is replaced with thymidine.

36. The isolated polynucleotide of claim 35, comprising a variant of nucleotides 46–360 of SEQ ID NO:1, wherein at position 342, guanosine is replaced with adenosine and wherein at position 348, cytidine is replaced with thymidine.

37. The isolated polynucleotide of claim 36, comprising a variant of SEQ ID NO:1, wherein at position 342, guanosine is replaced with adenosine and wherein at position 348, cytidine is replaced with thymidine.

38. An isolated polynucleotide, comprising a variant of nucleotides 274–360 of SEQ ID NO:1, wherein at positions 314 and 342, guanosine is replaced with adenosine and wherein at position 348, cytidine is replaced with thymidine.

39. The isolated polynucleotide of claim 38, comprising a variant of nucleotides 103–360 of SEQ ID NO:1, wherein at positions 314 and 342, guanosine is replaced with adenosine and wherein at position 348, cytidine is replaced with thymidine.

40. The isolated polynucleotide of claim 39, comprising a variant of nucleotides 49–360 of SEQ ID NO:1, wherein at positions 314 and 342, guanosine is replaced with adenosine and wherein at position 348, cytidine is replaced with thymidine.

41. The isolated polynucleotide of claim 40, comprising a variant of nucleotides 46–360 of SEQ ID NO:1, wherein at positions 314 and 342, guanosine is replaced with adenosine and wherein at position 348, cytidine is replaced with thymidine.

42. The isolated polynucleotide of claim 41, comprising a variant of SEQ ID NO:1, wherein at positions 314 and 342, guanosine is replaced with adenosine and wherein at position 348, cytidine is replaced with thymidine.

43. The isolated polynucleotide of claim 2, further comprising a heterologous polynucleotide.

44. The isolated polynucleotide of claim 43, wherein said heterologous polynucleotide encodes a heterologous polypeptide.

45. A method of producing a vector that comprises inserting the isolated polynucleotide of claim 2 into a vector.

46. A vector comprising the isolated polynucleotide of claim 2.

47. The vector of claim 46, wherein said polynucleotide is operably associated with a heterologous regulatory sequence.

48. A host cell comprising the isolated polynucleotide of claim 2.

49. The host cell of claim 48, wherein said isolated polynuclcotide is operably associated with a heterologous regulatory sequence.

50. A method of producing a polypeptide that comprises culturing the host cell of claim 49 under conditions such that said polypeptide is expressed, and recovering said polypeptide.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 426 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 46..360

(ix) FEATURE:

(A) NAME/KEY: sig_peptide
          (B) LOCATION: 46..100

(ix) FEATURE:
          (A) NAME/KEY: mat_peptide
          (B) LOCATION: 103..360

(xi) SEQUENCE DESCRIPTION: SEQ ID NO:1:

AAGAGCAGCA GCAGGGTGGG AGAGAAGCTC CAGTCAGCCC ACAAG ATG CCA TTG          54
                                                Met Pro Leu
                                                -19

TCC CCC GGC CTC CTG CTG CTG CTC TCC GGG GCC ACG GCC ACC GCT          102
Ser Pro Gly Leu Leu Leu Leu Leu Ser Gly Ala Thr Ala Thr Ala
    -15                 -10                 -5

GCC CTG CCC CTG GAG GGT GGC CCC ACC GGC CGA GAC AGC GAG CAT ATG      150
Ala Leu Pro Leu Glu Gly Gly Pro Thr Gly Arg Asp Ser Glu His Met
 1               5                  10                  15

CAG GAA GCG GCA GGA ATA AGG AAA AGC AGC CTC CTG ACT TTC CTC GCT      198
Gln Glu Ala Ala Gly Ile Arg Lys Ser Ser Leu Leu Thr Phe Leu Ala
                20                  25                  30

TGG TGG TTT GAG TGG ACC TCC CAG GCC AGT GCC GGG CCC CTC ATA GGA      246
Trp Trp Phe Glu Trp Thr Ser Gln Ala Ser Ala Gly Pro Leu Ile Gly
            35                  40                  45

GAG GAA GCC CGG GAG GTG GCC AGG CGG CAG GAA GGC GCA CCC CCC CAG      294
Glu Glu Ala Arg Glu Val Ala Arg Arg Gln Glu Gly Ala Pro Pro Gln
 50                  55                  60

CAA TCT GCG CGC CGG GAC AGA ATG CCC TGC AGG AAC TTC TTC TGG AAG      342
Gln Ser Ala Arg Arg Asp Arg Met Pro Cys Arg Asn Phe Phe Trp Lys
 65                  70                  75                  80

ACC TTC TCC TCC TGC AAA TAAAACCTCA CCCATGAATG CTCACGCAAG             390
Thr Phe Ser Ser Cys Lys
                85

TGTAATGACA GACCTGAATA AAATGTATTA AGCAGC                              426

(2) INFORMATION FOR SEQ ID NO:2:

(i) SEQUENCE CHARACTERISTICS:
         (A) LENGTH: 105 amino acids
         (B) TYPE: amino acid
         (D) TOPOLOGY: linear (ii) MOLECULE TYPE: protein (xi) SEQUENCE DESCRIPTION: SEQ ID NO:2:

Met Pro Leu Ser Pro Gly Leu Leu Leu Leu Leu Ser Gly Ala Thr
-19                 -15                 -10                 -5

Ala Thr Ala Ala Leu Pro Leu Glu Gly Gly Pro Thr Gly Arg Asp Ser
            1               5                  10

Glu His Met Gln Glu Ala Ala Gly Ile Arg Lys Ser Ser Leu Leu Thr
     15                  20                  25

Phe Leu Ala Trp Trp Phe Glu Trp Thr Ser Gln Ala Ser Ala Gly Pro
 30                  35                  40                  45

Leu Ile Gly Glu Glu Ala Arg Glu Val Ala Arg Arg Gln Glu Gly Ala
            50                  55                  60

Pro Pro Gln Gln Ser Ala Arg Arg Asp Arg Met Pro Cys Arg Asn Phe
            65                  70                  75

Phe Trp Lys Thr Phe Ser Ser Cys Lys
         80                  85

(2) INFORMATION FOR SEQ ID NO:3:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:3:

Met Gly Gly Cys Ser Thr Arg Gly Lys Arg Pro Ser Ala Leu Ser Leu
1               5                   10                  15

Leu Leu Leu Leu Leu Leu Ser Gly Ile Ala Ala Ser Ala Leu Pro Leu
                20                  25                  30

Glu Ser Gly Pro Thr Gly Gln Asp Ser Val Gln Asp Ala Thr Gly Gly
            35                  40                  45

Arg Arg Thr Gly Leu Leu Thr Phe Leu Ala Trp Trp His Glu Trp Ala
    50                  55                  60

Ser Gln Asp Ser Ser Ser Thr Ala Phe Glu Gly Gly Thr Pro Glu Leu
65              70                  75                  80

Ser Lys Arg Gln Glu Arg Pro Pro Leu Gln Gln Pro Pro His Arg Asp
                85                  90                  95

Lys Lys Pro Cys Lys Asn Phe Phe Trp Lys Thr Phe Ser Ser Cys Lys
                100                 105                 110

(2) INFORMATION FOR SEQ ID NO:4:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:4:

Gln Glu Gly Ala Pro Pro Gln Gln Ser Ala Arg Arg Asp Xaa Met Pro
1               5                   10                  15

Cys Arg Asn Phe Phe Trp Lys Thr Phe Ser Ser Cys Lys
                20                  25

(2) INFORMATION FOR SEQ ID NO:5:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

GACTGGATCC GCCATCATGC CATTGTCCCC CGGCC                                      35

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

GACTGGTACC GGTCTGTCAT TACACTTGC                                             29

(2) INFORMATION FOR SEQ ID NO:7:

(i) SEQUENCE CHARACTERISTICS:
  (A) LENGTH: 25 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:7:

```
GACTCCATGG CCCTGCCCCT GGAGG                                      25
```

(2) INFORMATION FOR SEQ ID NO:8:

(i) SEQUENCE CHARACTERISTICS:
  (A) LENGTH: 23 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:8:

```
AGATCTTTTG CAGGAGGAAA AGG                                        23
```

(2) INFORMATION FOR SEQ ID NO:9:

(i) SEQUENCE CHARACTERISTICS:
  (A) LENGTH: 411 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:9:

```
GGCAGAGGAT GTGCAGCAGC AGGGTGGGAG AGAAGCTCCA GTCAGCCCAC AAGATGCCAT    60
TGTCCCCCGG CCTCCTGNTG CTGCTGCTCT CCGGGGCCAC GGCCACCGCT GCCCTGCCCC   120
TGGAGGGTGG CCCCACCGGC CGAGAACAGC NAGCATATGC AGGAAGCGGC AGGAATAAGG   180
AAAAGCAGCC TCCTGACTTT CCTCGCTTGG TGGTTTGAGT GGACCTCCCA GGCCAGTNTC   240
GNGCCCCTCA TAAGGAGAGG AAGCCCGGGA AGGTTTGCCA GGNGGCAGGA NGGGCGCACC   300
CCCCCAGCAA TCTGCGGGGC CGGGTACAGA ATTGCCNTGC AGGAAATTTN TTTCTGGGAA   360
GANCTTTTTN CTGCTGGCAA ATAAAAACNT NAACCCATGA ATTNTTCAAG G            411
```

(2) INFORMATION FOR SEQ ID NO:10:

(i) SEQUENCE CHARACTERISTICS:
  (A) LENGTH: 302 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:10:

```
GGCACGAGCT CGGGCCAGCC AAGAACACTA CAAAGTTGAG CCGTGTGTCC TGTCCAAGCT    60
GTGAAGTGCA ACACACGTGC ACACACACAC ACCATGCAGG CCAAAAAGCC AACAAGAGAC   120
AGAGAGTGGG CTAGCGTGTG GCCACGTCGG GACTGTACTC ACCTCGCTGT CTCGGCCGGT   180
GGGGCCACCC TCCAGGGGNC AGGGCAGCGG TGGCCGTGGC CCCGGNAGAG CAGCAGCAGC   240
AGGNANGCCG GGGACAATG GNCATCTTGT GGGCTGACTG GAGCTTNTNT GCCCACCCTG    300
```

(2) INFORMATION FOR SEQ ID NO:11:

(i) SEQUENCE CHARACTERISTICS:
        (A) LENGTH: 456 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
TGCTGCTTAA TACATTTTAT TCAGGTCTGT CATTACACTT GCGTGAATNT CATCGGGTGA      60

GGTTTTATTT GCAGGAGGAG AAGGTCTTCC AGAAGAAGTT CCTGCAGGGC ATTCTGTCCC     120

GGCGCGCGGA TTGCTGGGGG GGTGCGCCTT CCTGCCGCCT TGNCACCTCC CGAGCTTCCT     180

CTCCTATGAG GGGCCCGGCA CTGGCCTGGG GAGGTCCACT CAAACCACCA AGCGAGGAAA     240

GTCAGGAGGC TGCTTTTCCT TATTCCTGCC GCTTCCTGCA TATGCTCGCT GTCTCGGCCG     300

GTGGGGCACC CTCCAGGGGC AGGGCAGCGG TGGCCGTGGC CCGGAAGAGC AGCAGCAGCA     360

GGAGGCCGGG GGACAATGGC ATCTTGTGGG CTGACTGGAA CTTCTCTCCC ANCCTGCTGC     420

TGCTCTTCCT TCCTGGCAGC CCTGAAATCA ATGTTT                               456
```